United States Patent [19]

Clark

[11] 4,016,264

[45] Apr. 5, 1977

[54] WART TREATMENT WITH PHOSPHONOACETIC ACID OR DERIVATIVES THEREOF

[75] Inventor: Leland L. Clark, Salt Lake City, Utah

[73] Assignee: The University of Utah, Salt Lake City, Utah

[22] Filed: July 14, 1975

[21] Appl. No.: 595,941

[52] U.S. Cl. .................................. 424/198; 424/61; 424/95; 424/212; 424/230; 424/234; 424/235

[51] Int. Cl.² ......................................... A61K 31/66

[58] Field of Search .............. 424/95, 61, 212, 230, 424/234, 235, 198

[56] References Cited

UNITED STATES PATENTS

| | | | |
|---|---|---|---|
| 1,951,737 | 3/1934 | Nitardy | 424/234 X |
| 2,025,399 | 12/1935 | Quisling | 424/234 X |
| 2,257,106 | 9/1941 | Christiansen | 424/234 X |
| 3,467,747 | 9/1969 | Hammaraskjold et al. | 424/234 |

*Primary Examiner*—Albert T. Meyers
*Assistant Examiner*—Vera C. Clarke

[57] ABSTRACT

A method and composition of matter for reducing warts with an active compound including phosphonoacetic acid, methylphosphonic acid and/or at least one of the physiologically acceptable sodium, potassium and calcium derivatives thereof and, if desired, a tissue penetrating and/or tissue removing agent. The method includes contacting a wart with the composition of this invention until the wart has been suitably reduced.

6 Claims, No Drawings

WART TREATMENT WITH PHOSPHONOACETIC ACID OR DERIVATIVES THEREOF

BACKGROUND

1. Field of the Invention

The present invention relates to a composition of matter and method for reducing warts.

2. The Prior Art

The wart is an epidermal eruption that has historically proven to be resistant to treatment and also transitory in nature. Probably the most vexatious of all warts, for example, other than those which constitute cosmetic blemishes, is the plantar wart, *verruca plantaris*, which occurs as a lesion in the thickened tissue on the sole of the foot. The plantar wart generally interferes with walking comfort and may even combine as an aggregate of contiguous plantar warts to form a mosaic wart thereby adding greatly to the discomfort of the victim.

Previous methods of wart treatment have included fulguration (destruction of the epidermal eruption tissue of the wart by electrolysis), surgical removal, or the application of various tissue removing agents including, for example, liquid nitrogen. Examples of other tissue removing agents include a keratolytic agent such as salicylic acid (o-hydroxybenzoic acid) and a blistering or vesicating agent such as cantharadin, (2, 3-dimethyl-7-oxybicyclo [2.2.1] heptane-2, 3-didicarboxylic anhydride).

It will be noted that in each of the foregoing prior art techniques for treating warts the technique involves the physical destruction of the epidermal tissue manifestation of the wart without necessarily attacking its underlying causative agent. As a result, it has been found that the epidermal eruption of the wart often returns, even after extensive and ofttimes painful treatment.

Successful wart treatment is further hampered by the requirement that the patient make frequent return visits to the treating physician. Accordingly, the patient finds this bothersome and often neglects to continue appropriate treatment resulting in treatment failure.

From the foregoing, it is readily apparent that successful wart treatment requires that the treatment involve suppression or, preferably, destruction of the underlying causative agent. The treatment should also be relatively rapid, painless, and effective when conducted by the user. Such a method of treatment and composition used in the method is disclosed in the present invention.

BRIEF SUMMARY AND OBJECTS OF THE INVENTION

The present invention incorporates an active compound including phosphonoacetic acid, methylphosphonic acid, and/or at least one of the physiologically acceptable sodium, potassium and calcium derivatives thereof in combination with a tissue penetrating and/or removing agent. This combination has been found to be surprisingly effective for treating warts. The tissue penetrating agent permits the active compound to reach the underlying causative agent. It is believed that the active compound inhibits replication of the wart causative agent. The tissue removing agent also serves to remove the outer epidermal protective layer over the wart causative agent.

The method includes incorporating the combination into a lotion or otherwise unctuous base, paste or as a plaster which is periodically applied to the wart.

It is therefore a primary object of this invention to provide improvements in treating warts.

Another object of this invention is to provide improvements in the method for treating warts.

It is another object of this invention to provide compositions of matter for treating warts.

These and other objects and features of the present invention will become more fully apparent from the following description and appended claims.

DETAILED DESCRIPTION OF THE PREFERRED EMBODIMENTS

Epidermal eruptions such as warts present to the physician and more particularly the dermatologist a perplexing problem of treatment not only due to the depth of penetration of the wart into the dermal layer but also its transitory nature. Although warts are occasionally subject to spontaneous regression, reliance on spontaneous regression is undesirable and, therefore, an unsatisfactory method of treatment. Warts that have spontaneously regressed also recur and have also been known to recur even after treatment by the prior art techniques.

Two principal features of the wart must be given consideration for wart treatment, (1) the external tissue eruption, if any, or overlying tissue and (2) the underlying causative agent. Attention directed to only the first feature, the tissue eruption, has apparently been the reason for the relatively poor success rate in prior art wart treatment methods. Without adequately attacking the underlying causative agent, the epidermal eruption of many warts are quickly reformed and must be again subjected to treatment.

Accordingly, successful wart treatment requires inhibition of replication of the underlying wart causative agent. The discovery has been made that an active compound including phosphonoacetic acid, methylphosphonic acid and the physiologically acceptable sodium, potassium and calcium derivatives thereof is surprisingly effective in inhibiting the replication of the underlying wart causative agent. Due to the caustic nature of phosphonoacetic acid, it is generally desirable to use methylphosphonic acid and other physiologically acceptable derivatives thereof including the sodium, potassium and calcium derivatives.

These active compounds may be set forth with the following structural formulas for the sodium derivatives. These are set forth below with the understanding that suitable compounds with potassium and calcium have also been found to be useful.

Phosphonoacetic acid, $(HO)_2POCH_3COOH$, has the following structural formula:

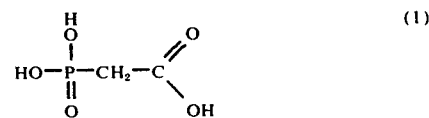

(1)

Phosphono sodium acetate, $(HO)_2POCH_3COONa$, has the following structural formula:

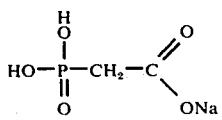

Methylphosphonic acid, CH₃O.P(OH)₂, has the following structural formula:

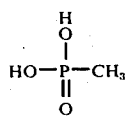

wherein the acetic acid group has been replaced by a methyl group;

Methyl sodium phosphonic acid, CH₃OPOHONa, has the following structure:

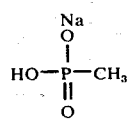

Methyl disodium phosphonic acid, CH₃OP(ONa)₂, has the following structure:

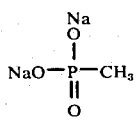

Similar phosphono compounds useful in the practice of this invention include also the potassium and calcium derivatives as stated hereinbefore.

It has also been found surprisingly beneficial to combine these active compounds with a tissue penetrating and/or a tissue removing agent so as to enhance the attack of the active compound on the wart underlying causative agent.

A tissue penetrating agent such as dimethylsulfoxide (hereinafter DMSO) and n-decylmethylsulfoxide, (hereinafter nDMSO) has been successfully incorporated with these active compounds with surprising beneficial results. It is believed that the DMSO or nDMSO acts as a penetrant for assisting the active compound in reaching the underlying wart causative agent.

A tissue removing agent such as a keratolytic agent is also useful since it removes the outer tissue layer of the wart to expose the wart causative agent to the action of the active compound. Tissue removing agents especially useful for this purpose preferentially include a keratolytic agent such as salicylic acid but may also involve a vesicating agent such as cantharadin. Although isolated instances of minor reddening of the tissue surrounding the wart has been experienced with these tissue removing agents, no long-term ill effects have been reported. Accordingly, reasonable precautions should always be exercised by the user to reduce contact and resulting adverse tissue reaction with normal tissue adjacent the wart.

In a number of instances, persons with a wart problem have been found to have more than one wart and not all warts were treated with equal success on the same person. For example, plantar warts on the ball of the foot have proven particularly difficult to treat primarily because of their location and the thickness of the overlying tissue. In those instances, greater personal attention by the attending physician is often required to accommodate successful treatment. It is also found occasionally necessary to couple the foregoing treatment with debridement for removal of the thickened tissue overlying the wart. In most other instances, patient administered treatment according to this invention has been found to be entirely adequate.

The following examples are given by way of illustration only and are not to be considered as limiting the scope of the claimed invention.

EXAMPLE 1

According to one presently preferred embodiment of the invention, a 5% aqueous solution of phosphonoacetic acid was prepared and had incorporated therewith a 5% solution of cantharadin. Solutions of phosphonoacetic acid ranging between 0.5 to 5.0% by weight were tried with greater success being obtained with the foregoing 5.0% solution. The combined solution was topically applied to the wart once a day for a period of at least one week. Following this treatment protocol, an outstanding ratio for removing warts was achieved as demonstrated in Table I, below.

TABLE I

Evaluation of Wart Removal by Phosphonoacetic Acid and Cantharadin

| No. of Patients | Previous treatment | Phosphonoacetic Acid/Cantharadin (% Wart Removed) |
| --- | --- | --- |
| 4 | 40% Salicylic Acid Plaster (Unsuccessful) | 100% |
| 3 | Liquid Nitrogen (Unsuccessful) | 100% |
| 4 | None | 100% |

Whether a vesicating agent such as cantharadin is used as the tissue removing agent or a keratolytic agent such as salicylic acid is used as the tissue removing agent in conjunction with the phosphonoacetic acid, each serves to remove overlying tissue and expose the underlying wart causative agent to the activity of the phosphonoacetic acid.

EXAMPLE 2

Another presently preferred embodiment of this invention involved a 10% suspension of phosphonoacetic acid in a volatile carrier such as acetone. This suspension was "painted" on the surface of a 40% salicylic acid plaster. Salicylic acid plasters are commercially available in a number of sizes and concentrations. For example, a 40% salicylic acid plaster is marketed by Duke Laboratories, Inc., South Norwalk, Conn. Evaporation of the carrier left a residue of phosphonoacetic acid on the surface of the salicylic acid plaster. The plaster was then applied directly to the wart with outstanding success as indicated in Table II, below.

TABLE II

Evaluation of Wart Removal by Phosphonoacetic Acid and Salicylic Acid

| No. of Patients | Previous Treatment | Phosphonoacetic Acid/ Salicylic Acid (% Wart Removal) |
|---|---|---|
| 2 | Liquid Nitrogen (Unsuccessful) | 80%–100% |
| 2 | Fulguration (Unsuccessful) | 80%–100% |
| 2 | Excision (Unsuccessful) | 100% |
| 3 | Liquid Nitrogen and Excision (Unsuccessful) | 70%–100% |
| 11 | None | 80%–100% |

Treatment was extended over a period from seven days to 21 days with replenishment of the composition on the wart being the responsibility of the patient. Variations in the percent wart removal were experienced and appear to be dependent upon a number of variables. These variables included time duration for treatment, location, and type of wart. Also, some patients had more than one wart, with each wart being treated with different degrees of success. In spite of these variables, the treatment method of this invention, as compared with the previous treatment techniques, appeared to be outstandingly successful.

EXAMPLE 3

Similar surprising results were obtained by incorporating 5% phosphonoacetic acid and 5% salicylic acid in a 5% glycerin lotion base. The use of a lotion base permitted the patient to be more directly involved in self-treatment since the medication could be replenished readily when observed necessary by the patient. Glycerin also appears to contribute to the treatment process by acting in conjunction with salicylic acid as a penetrant to assist the active compound in reaching the underlying causative agent. The glycerin may also be coupled with propylene glycol to provide a suitable cream base for the lotion.

EXAMPLE 4

Additional surprising results were obtained with a lotion having a 5% glycerin base which was prepared with 10% salicylic acid, 5% phosphonoacetic acid and 0.125% DMSO. The lotion was topically applied by the patient as required and resulted in complete eradication of the wart.

EXAMPLE 5

In order to obtain a broader spectrum analysis of the effectiveness of phosphonoacetic acid in combination with salicylic acid, salicylic acid ratios between 2 and 10% and phosphonoacetic acid ratios between 2 and 8% were tested at 2% increments each. At least 30 patients were tested in each group and all were treated successfully.

Since the phosphonoacetic acid is a relatively harsh compound to be applied directly to tissue, the various other active compounds were tested and also found effective, particularly the methyl and sodium, potassium, and calcium active compounds set forth hereinbefore. In most instances these were preferred although most of the initial testing was conducted with phosphonoacetic acid. Currently, the presently preferred composition includes (1) an active compound, (2) a penetrant, and (3) a keratolytic agent, which are all combined in a lotion, cream or other unctuous base, a portion of which, glycerin, appears to act also as a penetrant.

The penetrant ratio, particularly for a compound such as DMSO or nDMSO, is relatively low, for example, a ratio as low as 0.125% was found to be suitable.

The active compound, whether phosphonoacetic acid or methylphosphonic acid or the sodium, potassium or calcium derivatives thereof, was varied between about 2% to 8% of the total composition with about 5% found to be generally preferable.

The tissue removing agent generally preferred in practicing this invention was a keratolytic agent, preferably, salicylic acid. Salicylic acid ratios were varied between 2 and 10% of the composition with about 5% generally being preferred.

In each of the foregoing, the active compound was combined with other agents which assist the active compound in reaching the underlying wart causative agent. The active compound was tried alone for wart treatment with generally less satisfactory results, apparently because the overlying tissue served as a protective barrier for the wart causative agent.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for treating a wart comprising the steps of:
   contacting the wart with an effective amount of a composition comprising a suitable topical carrier, an effective amount of a tissue removing agent selected from the group consisting of salicylic acid and cantharadin and from about 0.5 to 8.0% by weight of a compound selected from the group consisting of phosphonoacetic acid, the sodium, potassium, and calcium salts of phosphonoacetic acid, methylphosphonic acid and the sodium, potassium, and calcium salts of methylphosphonic acid; and
   repeating the contacting step until the wart has been suitably treated.

2. The method as defined in claim 1 wherein the said carrier is an aqueous solution.

3. A method for treating a wart comprising:
   applying an effective amount of a composition topically to the wart, said composition containing a suitable topical carrier, from about 0.5% to 8.0% by weight of an active compound selected from the group consisting of phosphonoacetic acid, the sodium, potassium, and calcium salts of phosphonoacetic acid, methylphosphonic acid and the sodium, potassium, and calcium salts of methylphosphonic acid and an effective amount of at least one tissue treating agent selected from the group consisting of salicylic acid, cantharadin, dimethylsulfoxide, n-decylmethylsulfoxide, glycerin and a glycerin-salicylic acid mixture and;
   repeating the applying step until the wart has been suitably treated.

4. A composition of matter for treating warts comprising a suitable topical carrier, from about 0.5 to 8.0% by weight of an active compound selected from the group consisting of phosphonoacetic acid, the sodium, potassium, and calcium salts of phosphonoacetic acid, methylphosphonic acid and the sodium, potassium, and calcium salts of methylphosphonic acid, and an effective amount of at least one tissue treating agent selected from the group consisting of salicylic acid, cantharadin, dimethylsulfoxide, n-decylmethylsulfoxide, glycerin and a glycerin-salicylic acid mixture.

5. The composition of matter as defined in claim 4 wherein the carrier is an unctuous base.

6. A method for treating a wart comprising the steps of:
applying an effective amount of a treated surface of a salicylic acid plaster to the wart, said treated surface having been prepared by depositing thereon a suspension of about 0.5 to 10.0% by weight percent of a compound selected from the group consisting of phosphonoacetic acid, the sodium, potassium, and calcium salts of phosphonoacetic acid, methylphosphonic acid and the sodium, potassium, and calcium salts of methylphosphonic acid in a volatile carrier and evaporating the carrier from the surface of the salicylic acid plaster; and
repeating the said applying step until the wart has been suitably treated.

\* \* \* \* \*